(12) United States Patent
Diguet et al.

(10) Patent No.: US 9,200,164 B2
(45) Date of Patent: Dec. 1, 2015

(54) COATING SYSTEM

(75) Inventors: Sylvain Diguet, Basel (CH); Bruno Leuenberger, Basel (CH); Fabien Laboulfie, Basel (CH); Mehrdji Hémati, Basel (CH); Alain Lamure, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 97 days.

(21) Appl. No.: 13/579,120

(22) PCT Filed: Apr. 21, 2011

(86) PCT No.: PCT/EP2011/056420
§ 371 (c)(1),
(2), (4) Date: Dec. 3, 2012

(87) PCT Pub. No.: WO2011/134887
PCT Pub. Date: Nov. 3, 2011

(65) Prior Publication Data
US 2013/0189312 A1  Jul. 25, 2013

(30) Foreign Application Priority Data

Apr. 26, 2010 (CH) ........................................ 607/10

(51) Int. Cl.
| | | |
|---|---|---|
| *A61K 9/20* | (2006.01) | |
| *C09D 5/00* | (2006.01) | |
| *A23K 1/00* | (2006.01) | |
| *A23L 1/00* | (2006.01) | |
| *A23L 1/22* | (2006.01) | |
| *A61K 9/28* | (2006.01) | |

(52) U.S. Cl.
CPC . *C09D 5/00* (2013.01); *A23K 1/004* (2013.01); *A23L 1/0032* (2013.01); *A23L 1/22016* (2013.01); *A61K 9/2853* (2013.01); *A61K 9/2866* (2013.01)

(58) Field of Classification Search
None
See application file for complete search history.

(56) References Cited

U.S. PATENT DOCUMENTS

| 5,470,581 | A | 11/1995 | Grillo et al. | |
|---|---|---|---|---|
| 6,413,546 | B1 | 7/2002 | He et al. | |
| 6,787,156 | B1 * | 9/2004 | Bar-Shalom | 424/480 |
| 2002/0182275 | A1 | 12/2002 | He et al. | |
| 2006/0165794 | A1 | 7/2006 | Chenevier et al. | |
| 2010/0203134 | A1 | 8/2010 | Chenevier et al. | |
| 2010/0234313 | A1 * | 9/2010 | Hee et al. | 514/31 |

FOREIGN PATENT DOCUMENTS

| JP | 5-508667 | 12/1993 |
|---|---|---|
| JP | 7-87904 | 4/1995 |
| WO | WO 91/15578 | 10/1991 |
| WO | WO 00/54753 | 9/2000 |
| WO | WO 2004/030657 | 4/2004 |

OTHER PUBLICATIONS

International Search Report for PCT/EP2011/056420 mailed Jul. 18, 2011.
Written Opinion of the International Searching Authority mailed Jul. 18, 2011.
Japanese Office Action dated Nov. 4, 2014.

* cited by examiner

*Primary Examiner* — Snigdha Maewall
(74) *Attorney, Agent, or Firm* — Nixon & Vanderhye P.C.

(57) ABSTRACT

The present patent application relates to a novel coating system, coated compositions with such a coating system, as well as to the use of such compositions in the production food, feed, dietary supplements and/or pharmaceutical products, as well as to food, feed, dietary supplements and/or pharmaceutical products comprising such compositions.

19 Claims, 1 Drawing Sheet testing apparatus for the coating
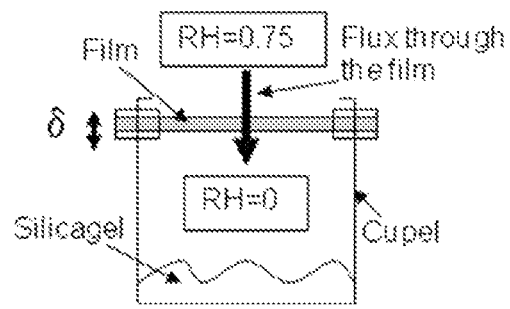

COATING SYSTEM

This application is the U.S. national phase of International Application No. PCT/EP2011/056420 filed 21 Apr. 2011 which designated the U.S. and claims priority to CH 607/10 filed 26 Apr. 2010, the entire contents of each of which are hereby incorporated by reference.

The present patent application relates to a novel coating system, wherein the coating comprises at least one lipid compound and at least one film forming compound and at least one plasticizer and/or at least one emulsifier, characterised in that the lipid compound has a mass median diameter (MMD) of less than 1 µm. Furthermore it relates to compositions coated with such a coating system and the use of such compositions in the production of food, feed, dietary supplements and/or pharmaceutical products.

The goal of the present invention was to find a coating system, which improves stability of the active ingredient(s), which are coated by such a coating system.

Surprisingly, it was found out that by using a coating system comprising
  (i) at least one lipid compound and
  (ii) at least one film forming compound and/or at least one emulsifier and
  (iii) at least one plasticizer,
characterised in that the mass median diameter of the lipid is less than 1 µm, improved coated compositions are obtained.

The compositions coated by a coating system according to the present invention are improved in regard to
  (a) storage stability;
  (b) sensory (smell and odour); (this is crucial when a strong tasting active ingredient is used);
  (c) control release of the active ingredient.

Therefore the present invention relates to a coating system comprising
  (i) at least one lipid compound and
  (ii) at least one film forming compound and/or at least one emulsifier and
  (iii) at least one plasticizer,
characterised in that the mass median diameter of the lipid is less than 1 µm, Mass Median Diameter or "MMD" is a measurement of the average particle size distribution. The results are expressed as diameters of the total volume distribution at 50% total throughflow. The mass median diameter (MMD) given in the present patent application are always measured by using a Malvern Mastersizer 2000. It is to be said that all particle sizes given in this patent application are average particles sizes. Monodispersity of the particles is not an essential criterion of the present invention.

The MMD of the lipid compound used in the coating of the composition according to the invention is less than 1 µm. Preferably, the MMD is below 0.95 µm, more preferably below 0.8 µm.

Preferred lipid compounds according to the present invention are saturated fatty acids as well as salts thereof, more preferred stearic acid or palmitic acid, as well as their salts. It is clear that one single lipid compound can be used as well as mixtures of two and more lipid compounds.

Preferred film forming compounds according to the present invention are hydrocolloids. The hydrocolloid can be either a polysaccharide or a protein. The term polysaccharides include gums (alginates, pectins, gum Arabic (gum Accacia))1, guar, caroube, xanthan), starches and modified starches, cellulose and cellulose derivatives like carboxymethylcellulose or hydroxypropylmethylcellulose. It is clear that one single film forming compound can be used as well as mixtures of two and more film forming compounds.

Preferred emulsifiers according to the present invention are sucrose ester, ascorbyl palmitate, polyoxyethylene-sorbitan-fatty acid esters (available under the trade name Tween). It is clear that one single emulsifier can be used as well as mixtures of two and more emulsifiers.

Preferred plasticizers according to the present invention are sugars like sucrose or a sugar derivative (mannitol, sorbitol), glycerol, mono- and diglyceride, acetylated monoglyceride, polyethylene glycol (PEG), polypropylene glycol. Preferably the PEG has a molecular weight between 200 and 6000. It is clear that one single plasticizer can be used as well as mixtures of two and more plasticizers.

The coating system can optionally comprise further components. These components can be useful for the production of the coating, the production of the coated composition, the production of the food, feed, dietary supplement or pharmaceutical product, or it can be added for other reasons. Such components can be e.g. dyestuffs, antioxidants, etc.

The coating system according to present invention preferably comprises 10 to 30 weight-percent (wt-%) of at least one lipid, preferably, 15 to 25 wt-%, based on the total weight of the coating system.

The coating system according to present invention preferably comprises 55 to 80 wt-% of at least one film forming compound and/or at least one emulsifier, preferably 60 to 75 wt-%, based on the total weight of the coating system.

The coating system according to present invention preferably comprises 5 to 25 wt-%, preferably 5 to 15 wt-% of at least one plasticizer, based on the total weight of the coating system. It is obvious than sum of the above mentioned percentages of the coating system always adds up to 100.

A coating system according to the present invention is used for coating an active ingredient (or a formulation comprising at least one active ingredient). Such a coated system comprises a core (comprising the active ingredient) and the coating system. The active ingredient which is coated is a fat soluble compound.

Therefore the present invention also relates to a composition comprising
  (a) a core, wherein the core comprises at least one fat soluble compound and
  (b) a coating system, comprising
    (i) at least one lipid compound and
    (ii) at least one film forming compound and/or at least one emulsifier and
    (iii) at least one plasticizer,
characterised in that the mass median diameter of the lipid is less than 1 µm.

All the preferences for the coating system apply to the above mentioned compositions.

At least one fat soluble compound is coated by the coating system according to the present invention. Preferably the fat soluble compound is a fat soluble vitamin or a PUFA (Poly Unsaturated Fatty Acid). Most preferred the fat soluble compound is a vitamin.

In addition the core can comprise further ingredients, usually additives, which are used in the production of such compounds or additives which are useful for products in which the compositions according to the present invention are incorporated. The core of the composition can be in any form. It can for example be in the form of beadlet comprising the active ingredient. A suitable beadlet, which can be coated by the coating system according to the present invention can be found in WO 2007/045488.

Furthermore the composition according to present invention comprises
  (i) 50 to 90 wt-%, based on the total weight of the composition, of core and
  (ii) 10 to 50 wt-%, based on the total weight of the composition, of coating system.

The coated compositions according to the present invention can be used in any kind of formulations, wherein the use of such fat soluble ingredients is useful. Usually such compositions can be used in food products. The food product can be in any form.

The coated compositions according to the present invention can also be used in feed products for animals such as poultry, pork, ruminants, etc. The feed product can be in any form.

The compositions according to the present invention can also be used as or used in dietary supplements. The dietary supplements can be in any form.

The coated compositions according to the present invention can also be used in pharmaceutical products. The pharmaceutical product can be in any galenical form, usually in the form of tablets.

A further embodiment of the present invention relates to food products, feed products, dietary supplements and/or pharmaceutical products, comprising at least one coated composition as defined above.

The invention is illustrated by the following Example. All temperatures are given in ° C. and all parts and percentages are related to the weight.

EXAMPLE 1

Step 1: Coating Formulation 450 g of deionised water are heated up to 80° C. 33.5 g Hydroxypropylmethylcellulose (HPMC) type methocel E19 are added and left at 80° C. for about 1 hour. The solution is then left overnight at room temperature for degassing. 6.5 g Polyethyleneglycol (PEG 400) are then added. 10 g of stearic acid are then predisperse in the HPMC/PEG solution. The micronisation of the stearic acid is then ensured by a dissolver disk type (ESCO-Labor, 1.5 Liter vessel, 60 mm diameter disk). In order to get a good micronisation of the stearic acid, it is necessary to be above the melting temperature (70-80° C.), and to put enough energy in the system (2000-4000 rpm). The cooling of the suspension must be quick (within a couple of minutes) and under strong agitation to avoid re-agglomeration of the stearic acid. 40 g of deionised water are then added to 210 g of the suspension to adjust the viscosity to about 400 mPa·s. The MMD of stearic acid in the suspension are measured with a Malvern Mastersizer 2000 at d3.2=0.26 μm, d10=0.15 μm, d50=0.30 μm, d90=0.59 μm.

Step 2: Application of the Coating Formulation on the Core Surface 80 g of a beadlet Vitamin A form (type Dry Vitamin A acetate 325 CWS/S) is fluidised in a small laboratory fluid bed equipment (DMR, WFP mini) and used as Core particles. 241 g of the coating formulation obtained in the step 1 is sprayed on the surface of the beadlets with a 2-fluid nozzle (air pressure: 2 bar) in a bottom-spray configuration. The spraying time is of about 3 hours with an inlet air temperature of 60° C. The final composition of the product obtained is:

TABLE 1

Compound of Example 1

| Ingredients | Wt-% |
|---|---|
| Dry Vitamin A acetate 325 CWS/S | 80 |
| HPMC | 13.4 |
| PEG 400 | 2.6 |
| Stearic acid | 4 |

EXAMPLE 2

In analogy to Example 1, a composition instead of using vitamin A acetate fish oil is used.

Step 1: Same Coating Formulation as in Example 1

Step 2: Application of the Coating Formulation on the Core Surface 85 g of a beadlet ROPUFA® '10' n-3 INF Powder is fluidised in a small laboratory fluid bed equipment (DMR, WFP mini) and used as Core particles. 181 g of the coating formulation obtained in the step 1 is sprayed on the surface of the beadlets with a 2-fluid nozzle (air pressure: 2.5 bars) in a bottom-spray configuration. The spraying time is of about 2.5 hours with an inlet air temperature of 60° C.

The final composition of the product obtained is:
The composition of the obtained product is then the following:

TABLE 2

Compound of Example 2

| Ingredients | Wt-% |
|---|---|
| ROPUFA® '10' n-3 INF Powder | 85 |
| HPMC | 10.1 |
| PEG 600 | 1.9 |
| Stearic acid | 3 |

Stability Test of the Coatings
Coating Water Permeability

Coatings were formed by spreading the solution on a glass plate with a manual handcoater CAMAG. The liquid coating was then dried in a ventilated oven at 40° C. during 24 hours.

The test facilities permit to create two atmospheres with different water humidity thanks to silicagel (RH=0) in a sealed bowl and sodium hydroxide (RH=0.75) in the closed environment around the bowl (FIG. 1). The gradient created generates a diffusion of the water through the coating. Bowl weight measured as function of the time (water uptake) gives the flux of water vapour through the film.

The water vapour permeability (WVP) is defined as:

$$WVP = \frac{\Delta m \cdot \delta}{A \cdot \Delta P \cdot \Delta t}$$

unit g·mm/(day·m² ·kPa)

Where $\Delta m$ (g) is the mass of water retains is the bowl during $\Delta t$ (day), $\delta$ the thickness of the coating (mm), A the surface of exchange (m²) and $\Delta P$ the difference of partial pressure of water (kPa) once the steady state has been reached. The lower the WVP, the better is the coating to protect the active against humidity.

The composition of coatings is the same as in Example 1 and 2.

Coating 1 comprises stearic acid, which has a MMD of 10 to 20 μm (Comparative example) and Coating 2 comprises stearic acid with a MMD of less than 1 μm (Invention).

| Ingredients | coating 1 | coating 2 |
|---|---|---|
| HPMC | 67 wt-% | 67 wt-% |
| PEG 600d | 13 wt-% | 13 wt-% |
| Stearic acid | 20 wt-% | 20 wt-% |
| MMD of Stearic acid | 10 to 20 μm | <1 μm |
| WVP | 1.42 | 0.18 |

The WVP has been reduced by a factor 7 to 8 by the micronisation of the stearic acid.

The invention claimed is:

1. A coating system comprising:
   (i) a lipid compound which is at least one selected from the group consisting of stearic acid, palmitic acid and salts thereof,
   (ii) at least one film forming compound and/or at least one emulsifier, and
   (iii) at least one plasticizer, wherein
   the lipid compound has a mass median diameter of less than 1 μm.

2. The coating system according to claim 1, wherein the mass median diameter of the at least one lipid compound is below 0.95 μm.

3. The coating system according to claim 1, wherein the mass median diameter of the at least one lipid compound is below 0.8 μm.

4. The coating system according to claim 1, wherein the at least one film forming compound is a hydrocolloid.

5. The coating system according to claim 1, which comprises at least one emulsifier selected from the group consisting of sucrose esters, ascorbyl palmitates and polyoxyethylene-sorbitan-fatty acid esters.

6. The coating system according to claim 1, wherein the plasticizer is at least one selected from the group consisting of sugars, glycerol, mono- and diglyceride, acetylated monoglyceride, polyethylene glycol, and polypropylene glycol.

7. The coating system according to claim 1, wherein the coating system comprises at least one further component.

8. The coating system according to claim 1, wherein the coating system comprises 10 to 30 wt-% of the at least one lipid, based on the total weight of the coating system.

9. The coating system according to claim 1, wherein the coating system comprises 55 to 80 wt-% of the at least one film forming compound and/or the at least one emulsifier, based on the total weight of the coating system.

10. The coating system according to claim 1, wherein the coating system comprises 5 to 25 wt-% of the at least one plasticizer, based on the total weight of the coating system.

11. A composition comprising:
    (a) a core which comprises at least one fat soluble compound, and
    (b) a coating system according to claim 1.

12. The composition according to claim 11, wherein the composition comprises:
    50 to 90 wt-%, based on the total weight of the composition, of the core, and
    10 to 50 wt-%, based on the total weight of the composition, of the coating system.

13. The composition according to claim 11, wherein the fat soluble compound is a fat soluble vitamin or a polyunsaturated fatty acid (PUFA).

14. The composition according to claim 11, comprising at least one further ingredient.

15. A food product, feed product, dietary supplement and/or pharmaceutical product, comprising the composition according to claim 11.

16. The coating system according to claim 4, wherein the hydrocolloid is at least one selected from the group consisting of polysaccharides and proteins.

17. The coating system according to claim 8, wherein the coating system comprises 15 to 25 wt-% of the at least one lipid, based on the total weight of the coating system.

18. The coating system according to claim 9, wherein the coating system comprises 60 to 75 wt-% of the at least one film forming compound and/or the at least one emulsifier, based on the total weight of the coating system.

19. The coating system according to claim 10, wherein the coating system comprises 5 to 15 wt-% of the at least one plasticizer, based on the total weight of the coating system.

* * * * *